United States Patent
Prochazka (10) Patent No.: US 9,198,843 B2
(45) Date of Patent: Dec. 1, 2015

(54) PROCESS FOR MANUFACTURING OF HIGH SURFACE AREA USP GRADE NANO-ANATASE BASE

(76) Inventor: Jan R Prochazka, Reno, NV (US)

(*) Notice: Subject to any disclaimer, the term of this patent is extended or adjusted under 35 U.S.C. 154(b) by 891 days.

(21) Appl. No.: 12/462,821

(22) Filed: Aug. 11, 2009

(65) Prior Publication Data

US 2010/0150852 A1 Jun. 17, 2010

Related U.S. Application Data

(60) Provisional application No. 61/188,601, filed on Aug. 11, 2008.

(51) Int. Cl.

| | |
|---|---|
| A61K 8/29 | (2006.01) |
| A61Q 17/04 | (2006.01) |
| B82Y 5/00 | (2011.01) |
| A61K 8/02 | (2006.01) |
| C01G 23/047 | (2006.01) |
| C01G 23/053 | (2006.01) |
| C01G 23/08 | (2006.01) |

(52) U.S. Cl.
CPC ............... *A61K 8/29* (2013.01); *A61K 8/0241* (2013.01); *A61Q 17/04* (2013.01); *B82Y 5/00* (2013.01); *C01G 23/047* (2013.01); *C01G 23/053* (2013.01); *C01G 23/08* (2013.01); *A61K 2800/413* (2013.01); *A61K 2800/651* (2013.01); *C01P 2004/64* (2013.01)

(58) Field of Classification Search
None
See application file for complete search history.

(56) References Cited

U.S. PATENT DOCUMENTS

| | | | | |
|---|---|---|---|---|
| 3,063,807 | A * | 11/1962 | Kenworthy | 423/70 |
| 3,615,204 | A * | 10/1971 | Libera et al. | 423/85 |
| 5,476,643 | A * | 12/1995 | Fogel | 423/610 |
| 6,261,713 | B1 * | 7/2001 | Walele et al. | 429/54 |
| 6,548,039 | B1 * | 4/2003 | Duyvesteyn et al. | 423/610 |
| 2008/0045410 | A1 * | 2/2008 | Prochazka et al. | 502/208 |

FOREIGN PATENT DOCUMENTS

EP 782971 A1 * 7/1997

* cited by examiner

*Primary Examiner* — Melvin C Mayes
*Assistant Examiner* — Colin W Slifka (57) ABSTRACT

The present invention provides a novel manufacturing process for producing a high surface area USP grade titanium dioxide in the nano-anatase form. In a manufacturing method aspect of the present invention, a process of producing a high surface area USP grade $TiO_2$ nano-anatase base is provided. The method involves steps of: a) phosphorus doping of the titanium hydrate obtained in hydrolysis of a titanium compound; b) drying and calcination of the doped paste, thereby producing a high surface area USP grade titanium dioxide in the anatase crystal form with nano-particles suitable for UV screens and cosmetics.

7 Claims, 8 Drawing Sheets

PROCESS FOR MANUFACTURING OF HIGH SURFACE AREA USP GRADE NANO-ANATASE BASE

This application claiming priority to U.S. provisional application No. 61/188,601 filed on Aug. 11, 2008.

FIELD OF THE INVENTION

The present invention is generally directed to the manufacturing of USP grade titanium dioxide in the anatase crystal form. More specifically it is directed to a manufacturing process producing high surface area USP grade titanium dioxide anatase nano-particles derived from the process, which are suitable for use in sun screen lotions, cosmetics and products requiring high level of optical transparency to the visible light.

BACKGROUND OF THE INVENTION

Titanium dioxide is known in many different crystal forms but only three of them are commonly found in the nature—rutile, anatase and brookite.

Nanosized titanium dioxide is a material of an increasing importance in the cosmetic industry. Nano-$TiO_2$ is perfectly inert and its special characteristics, such as absorption of UV light, make it a desirable material in UV screen lotions and other cosmetic products. It is often used in combination with nano-sized zinc oxide which also absorbs UV light.

Small particle size of $TiO_2$ is critical for the optical transparency of the products. Particles above 70 nm in size scatter visible light causing the "white nose" effect.

While the USP grade (meeting the United States Pharmacopeia specifications), nanosized rutile has been used in the cosmetic lotions for over a decade, the use of anatase and brookite has been limited. The thermodynamically stable rutile can be manufactured with the particle size in the required nano-range, meeting the desired USP specifications at the same time. Nano-rutile is produced by several industrial processes, for example by the diluted gas phase chloride process or via titanates.

Anatase and brookite are thermodynamically unstable. Particles of anatase rapidly sinter, and the particle size distribution is quickly moving outside the nano-range at temperature higher than 600° C. There is a noticeable conversion of nano-anatase into large rutile crystals above this temperature.

Large particle size and high volume of volatiles are two major technical obstructions that disqualify the anatase crystalline materials from UV screens and other cosmetic applications. The existing USP grade anatase pigment products are heavily sintered into large aggregates of about 300 nm in size. Generally, particles in these products are by one order of magnitude larger than is the desirable size for the UV screens in cosmetics. Light scattering on these pigmentary particles eliminates the materials from UV screen applications requiring the optical transparency in the visible light. Additionally, they are often contaminated by a fraction of pigmentary rutile.

Nanosized anatase made by the low-temperature processes contains usually a significant portion of volatile impurities. It is common that materials processed at 500° C. show 5 percent weight loss when heated to 800° C. Materials prepared at 350° C. may have over 20 weight percent of volatiles, while the USP limit is only one weight percent. The USP product must be over 99 percent titanium dioxide, showing less than 1 weight percent loss on the ignition at 800° C. for 2 hours (LOI).

For these reasons, manufacturing of a pure high surface nano-anatase meeting the USP specifications in the desired quality was not possible.

An object of the present invention is to provide a manufacturing method for production of USP grade high surface area nano-anatase base. A further object is to provide the USP grade nano-anatase base suitable for sun screens and cosmetic products.

SUMMARY OF THE INVENTION

The present invention provides an economical process for production of a high surface area titanium dioxide USP grade nano-anatase base, which can further be modified and used as the UV filter in the cosmetic products. This product can also be utilized as an UV protective material in applications requiring the optical transparency in the visible light (e.g. epoxy, plastics and resin filler).

In a method aspect of the present invention, a process of producing a high surface area USP grade titanium dioxide base, consisting of nano-particles in the anatase crystal form, is provided.

The process involves the steps of: a) introducing phosphorus doping agent to the wet or dry titanium hydrate [$Ti(OH)_4$], obtained preferably by hydrolysis of titanium sulphate or oxysulphate, wherein the phosphorus doping agent is phosphoric acid, a mineral acid containing phosphorus in the molecule, an inorganic or organic water soluble phosphate, or an inorganic or organic water soluble compound containing phosphorus in the molecule, wherein the concentration of phosphorus is in the range from 0.1 to 0.5 weight percent on the $TiO_2$ basis, providing a P-doped intermediate product; b) drying of the P-doped intermediate product and calcination in the temperature range from 600 to 900° C. for a time period 1 to 24 hours, thereby producing a high surface area USP grade nano-anatase base.

In the product aspect of the present invention, a USP grade nanoanatase base with the specific surface area greater than 20 $m^2$/g and smaller than 75 $m^2$/g, determined from the nitrogen adsorption and desorption isotherms at 77 K by the BET method, is provided. The USP base weight loss on ignition at 800° C. for 2 hours is smaller than 1 weight percent. The average particle size of the USP base, determined from the X-Ray diffraction crystal domain size using the Scherrer equation, is smaller than 40 nm and greater than 15 nm.

The USP base is further dispersed by wet milling, surface treated to block the photocatalytic activity of titanium dioxide, and optionally dried and micronized to achieve the desired morphology of the powder product.

The dispersion of the surface treated product or the dry and optionally micronized powder are re-dispersed in alkyl benzoate, oil, or another organic or aqueous media to make a ready-to-use intermediate product for cosmetics or applications requiring high optical transparency in the visible light.

DETAILED DESCRIPTION OF THE INVENTION

Present invention provides a method for economical mass-production of TiO$_2$ USP grade base consisting of nanoparticles of anatase. The method is particularly suitable for the sulfate process used for the production of the TiO$_2$ pigment; however, any other source of the titanium hydrate, such as titanium hydrate originating from the hydrolysis of titanium chloride or oxychloride, can be used.

Figure 1:
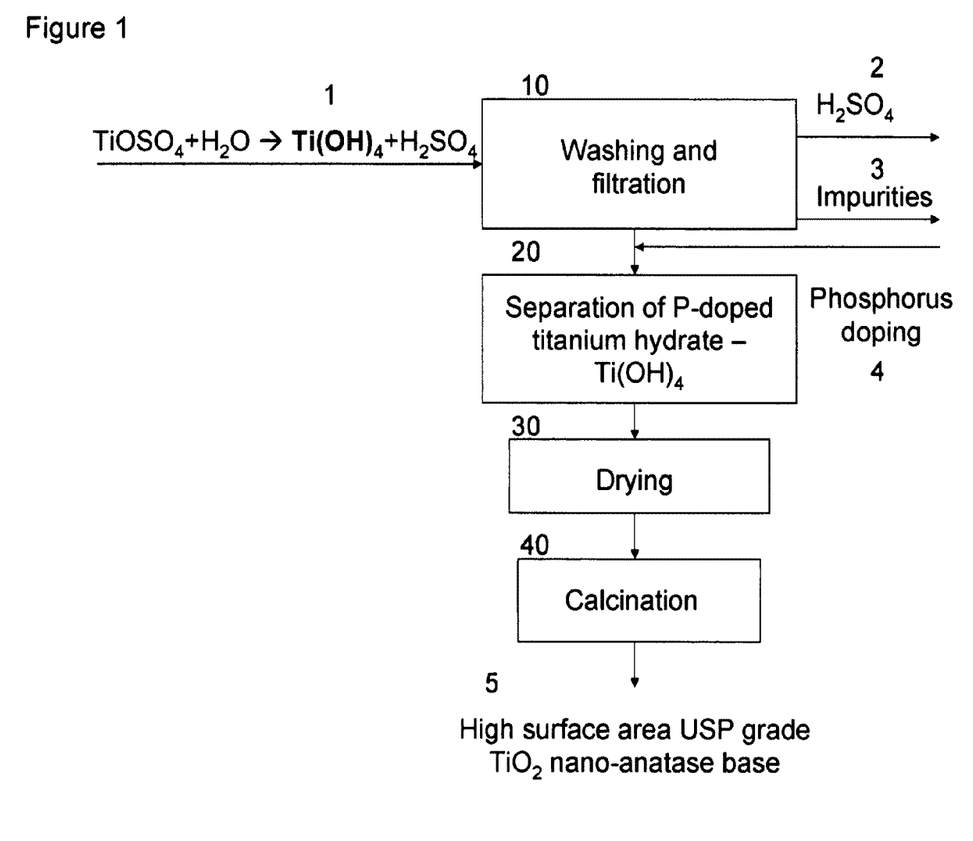
FIG. 1. is a general flow sheet, showing the steps of one embodiment of the process of the present invention, where the product is the high surface area USP grade nano-anatase base.

The method of the present invention is generally described in reference to FIG. 1. The flow sheet illustrates manufacturing of the USP nano-anatase base starting with the hydrolysis of titanium oxysulfate, making titanium hydrate (1), cleaning the titanium hydrate [Ti(OH)$_4$] from the sulfuric acid (2), iron and other impurities (3), in the repetitive washing and filtration step (10), where the titanium hydrate cake is re-pulped several times and washed with diluted sulfuric acid and deionized water.

Phosphorus doping agent (4) is then introduced to the washed titanium hydrate. Usually, the phosphorus doping agent is uniformly mixed into the clean titanium hydrate paste during the last re-pulping step (10), producing the P-doped intermediate product. Subsequently this P-doped intermediate product is separated from the slurry (20). Most often the separation occurs in the last filtration cycle of the step (10). The step (20) is often identical with the last cycle of the step (10). The introduced concentration of phosphorus is in the range from 0.1 to 0.5 weight percent on the TiO$_2$ basis. Optimally the phosphorus concentration is between 0.4 and 0.45 weight percent on the TiO$_2$ basis. Phosphoric acid is mainly used as the phosphorus doping agent.

Doping of a dry titanium hydrate is also possible.

The P-doped intermediate product is then dried (30). Drying of the filtered paste of the P-doped intermediate occurs preferably in the first zone of a rotary calciner just before it enters the calcination zone. The P-doped titanium hydrate slurry can also be dried without the previous filtration. In this case, drying is preferably conducted in a spray drying operation.

The dried P-doped intermediate product is then calcined (40) in the temperature range of 600-900° C. for the time period 1 to 24 hours producing the high surface area USP nano-anatase base (5). The specific surface area of the USP base, determined from the adsorption isothermes and calculated by the BET method, is greater than 20 m$^2$/g and smaller than 75 m$^2$/g. Most often the specific area of the USP base is between 25 and 30 m$^2$/g. The average particle size of the individual TiO$_2$ crystals is greater than 15 nm and smaller than 40 nm, determined from the XRD crystal domain size using the Scherrer equation. Typically the average particle size is the between 20 and 30 nm.

Figure 2:
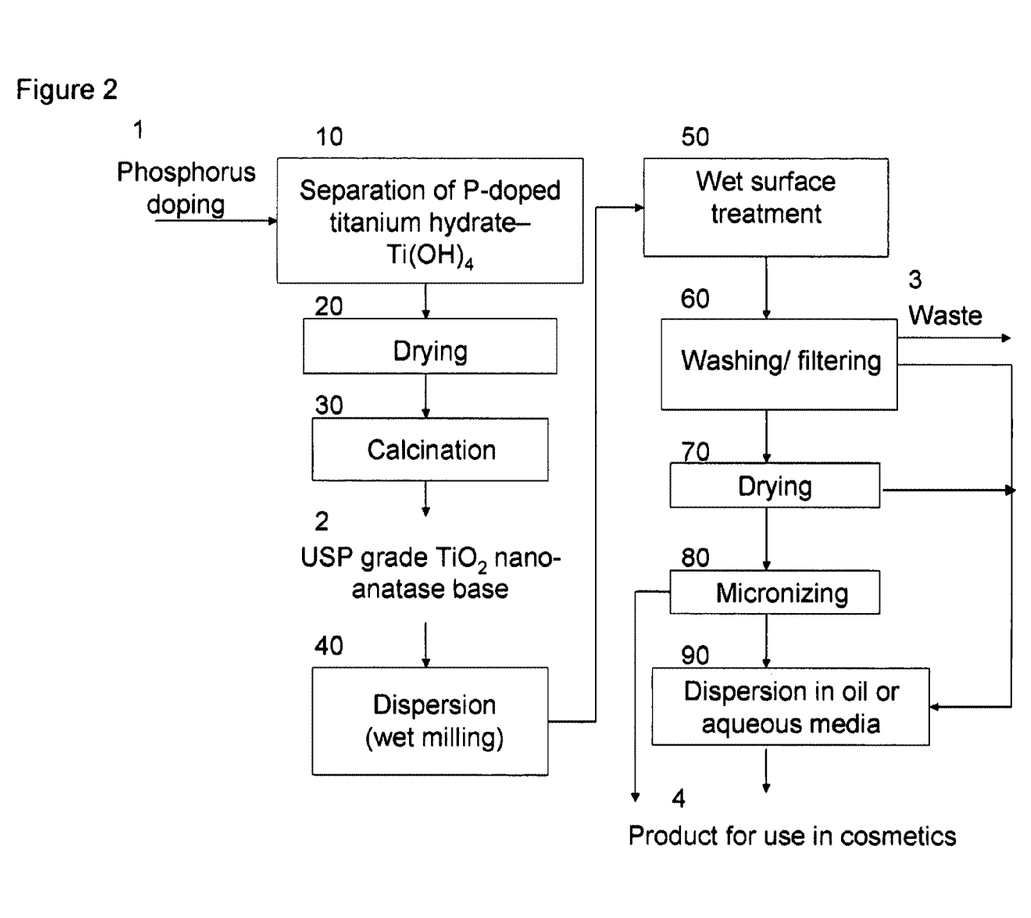
FIG. 2. is a general flow sheet, showing the steps of another embodiment of the process of the present invention, where the USP grade nano-anatase base is further processed to obtain a desirable intermediate product that can be incorporated into the cosmetic products as an UV screen.

The flow sheet in FIG. 2 describes the addition of the phosphorus doping agent (1) to the titanium hydrate paste, obtainable by the hydrolysis of titanium oxysulfate, separation (10) and drying (20) of the P-doped intermediate, and calcination of the dried product (30). The calcination occurs in the temperature range from 600 to 900° C. for the time period 1 to 24 hours. Typically the calcination conditions are between 700° C. and 850° C. for 2 to 10 hours.

The high surface USP nano-anatase base (2) is further processed in wet milling with the ceramic milling media, such as zirconia beads. Organic or inorganic surfactants are used in order to break the nano-anatase aggregates. The dispersed slurry of mostly individual particles contains less than 5 percent of oversized aggregates larger than 100 nm (40). The TiO$_2$ specific surface area significantly increases during the milling procedure. In some cases it can be the double.

The slurry of milled particles is further surface treated with silica and alumina to block the photocatalytic activity of TiO$_2$ (50). The coating is usually achieved by a slow deposition process during co-addition of hydrochloric acid and sodium silicate or sodium aluminate. The coating temperature is slightly below the boiling point of water, typically 80-95° C.

The surface treatment may involve alkyl silanes in combination with the silica-alumina coating, or without it. Silane surface treatment is often provided during the wet milling of the USP base, where the silane is used as the dispersant.

The surface treated USP base is then washed to remove all side-products from the surface treatment. Typically, a rotary filter combining the filtering procedure with the washing is used (60). The washed and filtered product is further dried (70), micronized (80) and re-dispersed (90) in alkyl benzoate, oil, milk or other media to receive a ready-to-use product for cosmetics (4).

The micronized product can often be re-dispersed directly in the cosmetic product. The wet paste obtained in the step (60) can also be directly incorporated into the cosmetic products, such as body milk, by redispersion of the wet coated USP material in the cosmetic composition.

The following examples illustrate, but do not limit, the present invention.

EXAMPLE 1

Figure 3:
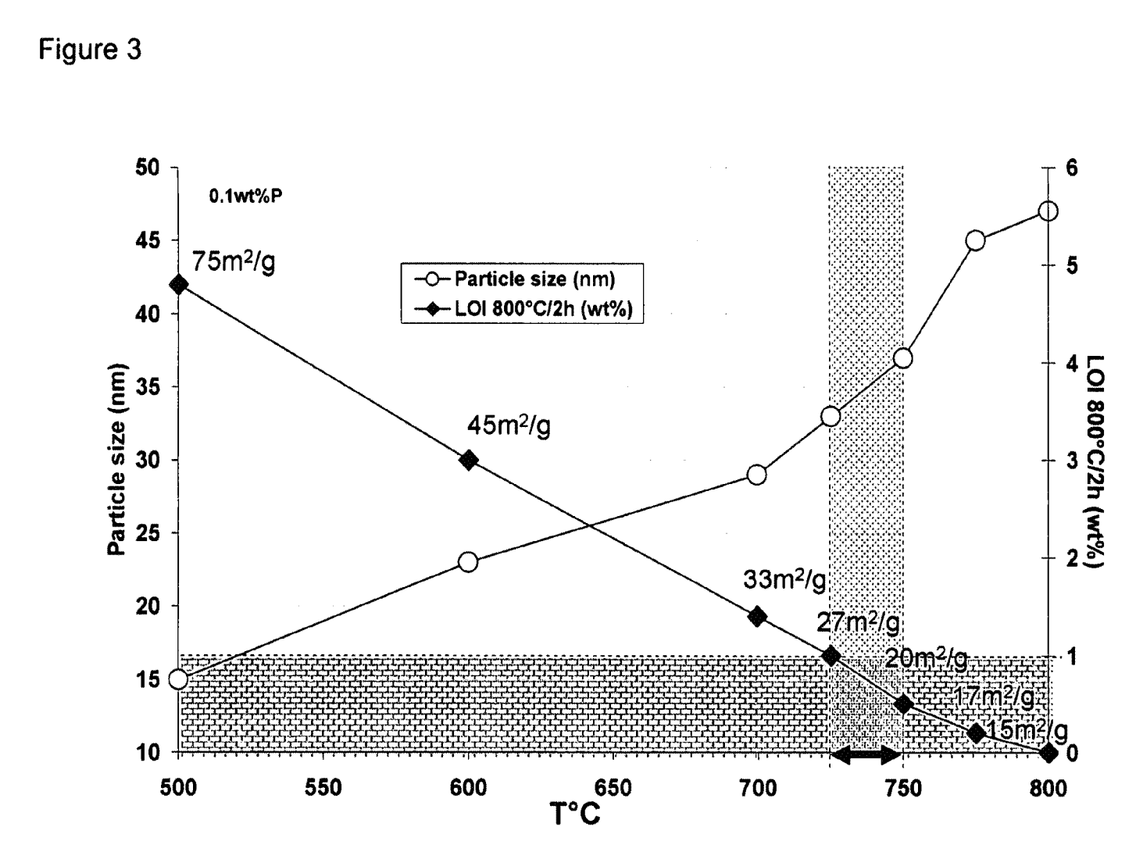
FIG. 3. shows a graph describing the original particle size and the specific surface area of the 0.1 weight percent phosphorus doped nano-anatase, produced at different temperatures in the range 500-800° C. It expresses the weight loss on ignition of these materials at 800° C. for 2 hours.

Titanium hydrate paste was treated with 0.1M phosphoric acid to adjust the concentration of phosphorus in the TiO$_2$ material to 0.1 weight percent. The doped paste was mixed well and then dried. The dried intermediate was subsequently calcined at 500, 600, 700 and 800° C. for 10 hours. The calcined samples were analyzed using the required USP procedures. Further the samples were evaluated for the particle size and the particle size distribution to determine suitability of the materials for the sun screens and applications requiring optical transparency. FIG. 3 shows a plot with the results. Importantly, materials with the small particle size did not pass the criteria of the weight loss on ignition at 800° C. Materials meeting the USP specifications were too coarse and heavily sintered into large aggregates to suit the cosmetic applications. There was only a narrow window of the calcination conditions between 725-750° C. at the 10 hour calcination time, producing the USP nano-base.

EXAMPLE 2

Figure 4:
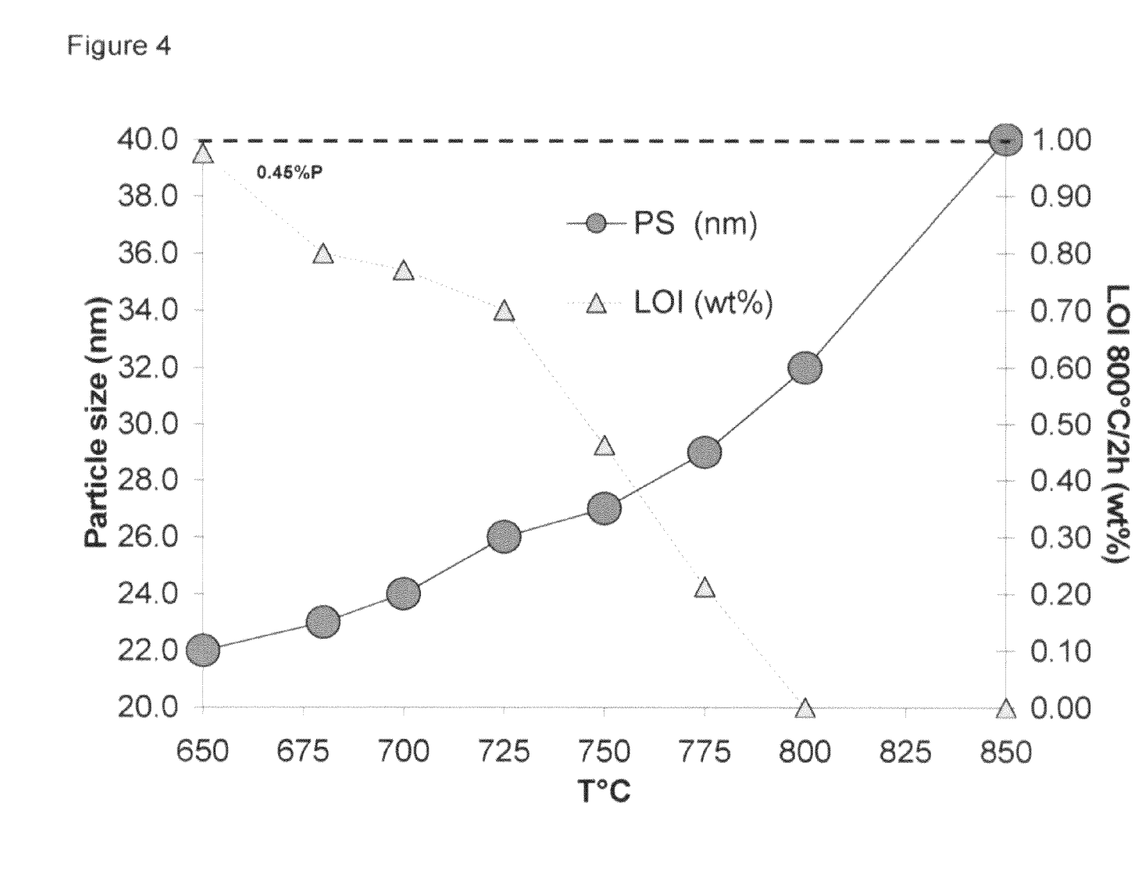
FIG. 4. shows a graph describing the particle size development of the 0.45 weight percent phosphorus doped nano-anatase, produced at different temperatures in the range 650-850° C., and their weight loss on ignition at 800° C. for 2 hours.
Figure 5:
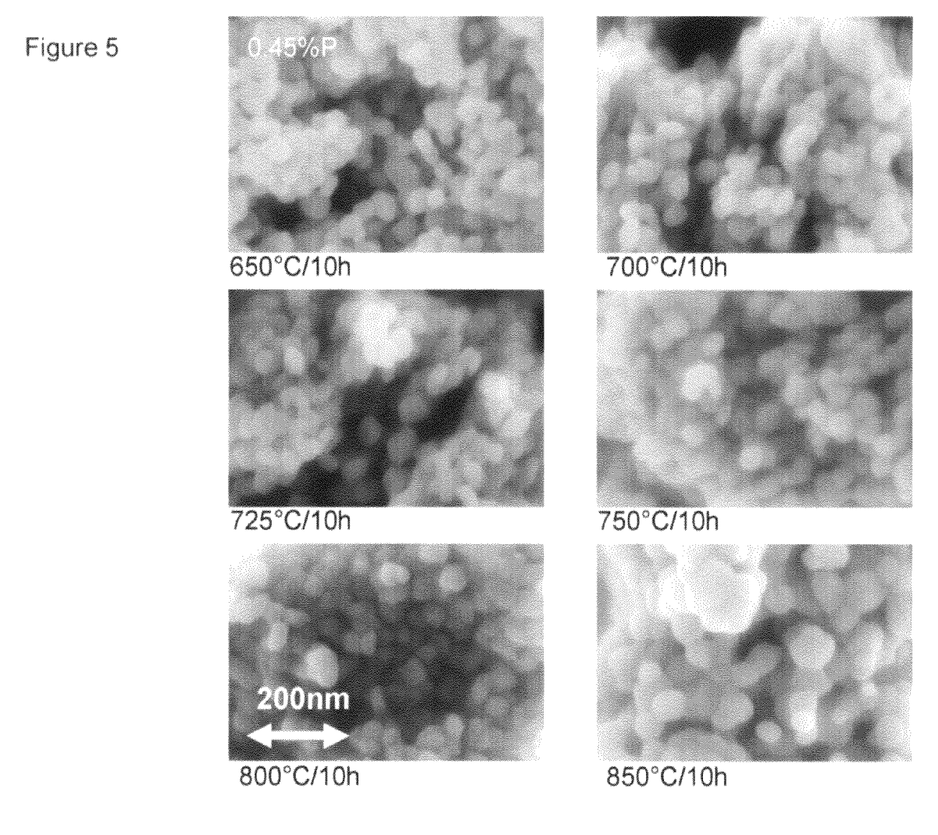
FIG. 5. shows scanning electron microscope images of the nano-anatase USP base materials with the 0.45 weight percent of phosphorus content on the TiO$_2$ basis, prepared in the temperature range 650 to 850° C.

Titanium hydrate paste was treated with 1M phosphoric acid to adjust concentration of phosphorus in the $TiO_2$ material to 0.45 weight percent. The doped paste was mixed well and dried. The dried intermediate was subsequently calcined at 650, 675, 700, 725, 750, 775, 800 and 850° C. for 10 hours. The calcined samples were analyzed according to the required USP analytical procedures. Further the samples were evaluated for the particle size and the particle size distribution to determine suitability of the materials for sun screen cosmetics and applications requiring optical transparency to the visible light. FIG. 4 shows a plot with the results. The materials all met the USP specifications. The weight loss on ignition at 800° C. (LOI) was less than 1 weight percent for all materials, including the 650° C. sample. The particle size was optimal for use in transparent cosmetics. The 850° C. material is already fused into coarser aggregates. Corresponding SEM pictures of the products are in FIG. 5. The particle size does not change much with the temperature. Shortening of the 850° C. calcination time can produce the USP base with the particle size distribution better suitable for cosmetics. The 650° C. material with the specific surface area of 50 $m^2/g$ and the particle size around 20 nm represents the lower limit of this production technique.

The low weight loss effect is not completely understood. The low loss on ignition at 800° C. of materials made at temperatures lower than 700° C. must be somehow associated with the content of phosphorus.

EXAMPLE 3

Figure 6:
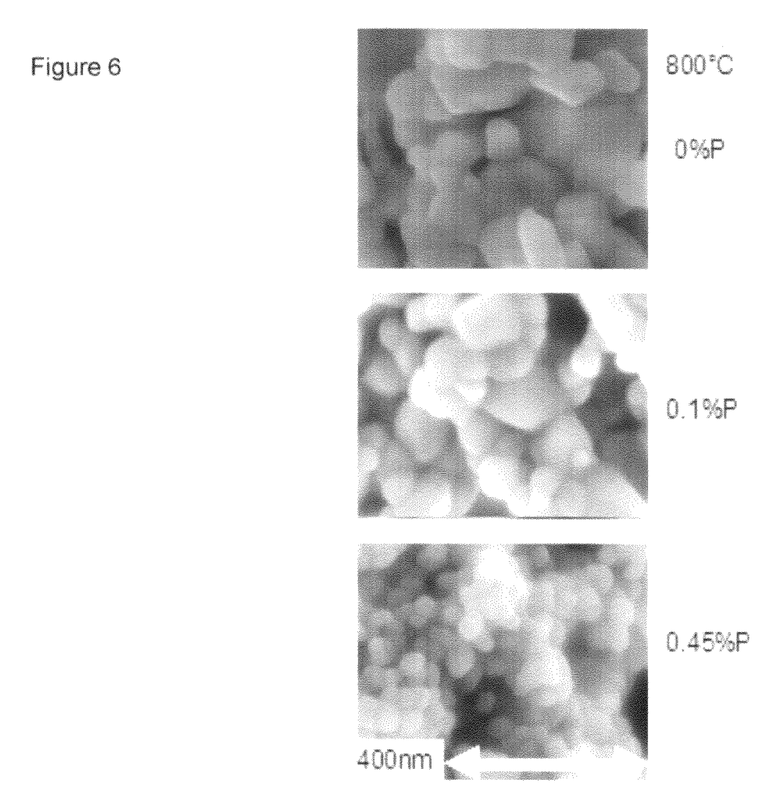
FIG. 6. shows scanning electron microscope images of anatase with different phosphorus content of 0.00; 0.10 and 0.45 weight percent after the LOI (loss on ignition) test at 800° C. for 2 hours.

Titanium hydrate paste was treated with diluted phosphoric acid to adjust the concentration of phosphorus to 0.3 weight percent in the $TiO_2$ material. The doped paste was mixed well and then dried. The dried intermediate was subsequently calcined at 500, 600, 700, 725 and 800° C. for 10 hours. The calcined samples were analyzed according to the required USP analytical procedures. Further, the samples were evaluated for the particle size and particle size distribution to determine suitability of the materials for applications requiring optical transparency to the visible light. Materials calcined above 700° C. all met the USP specifications and their particle size was suitable for their use in cosmetics. Materials calcined at 700° C. and lower did not meet the USP specifications. They did not pass the criteria of the weight loss on the ignition at 800° C. FIG. 6 shows SEM images of materials prepared in 700° C./10 hour calcination with different concentrations of phosphorus after the weight loss on ignition at 800° C. for 2 hour test (LOI). The impact of phosphorus on the particle size and aggregation of materials is significant.

EXAMPLE 4

Figure 7:
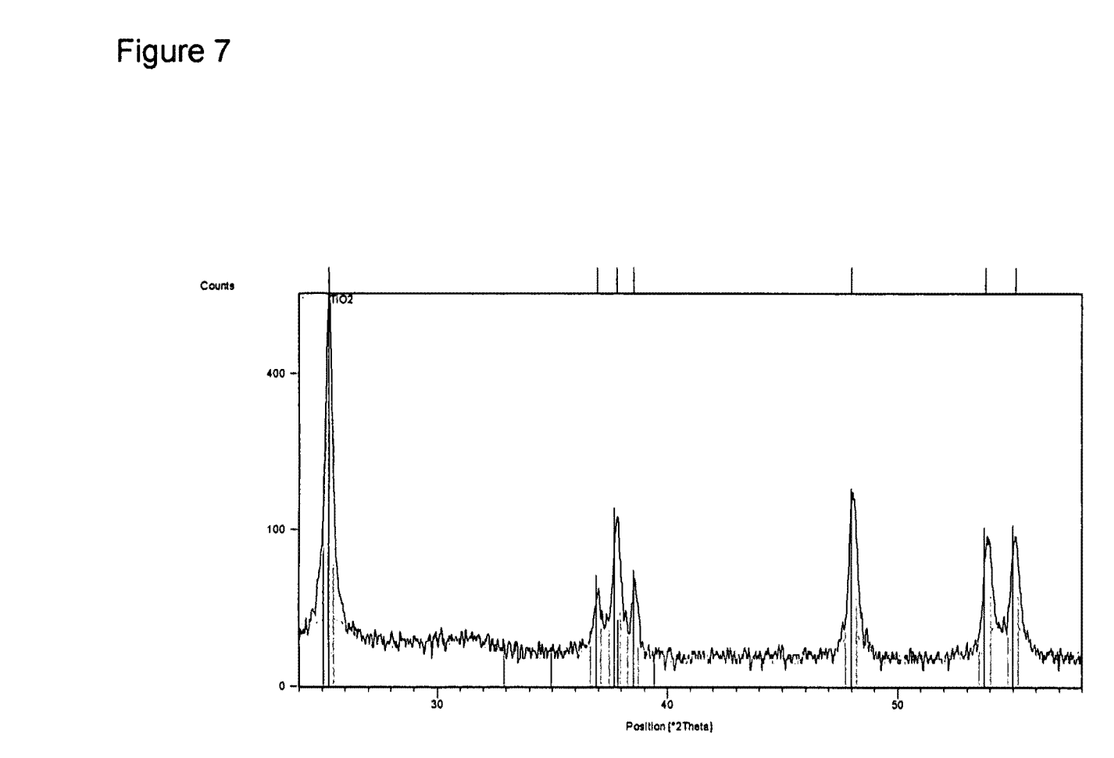
FIG. 7. shows the X-ray diffraction (XRD) pattern of the USP nano-anatase base doped with 0.3 weight percent of phosphorus on the TiO$_2$ basis, prepared at 720° C./10 hours.
Figure 8:
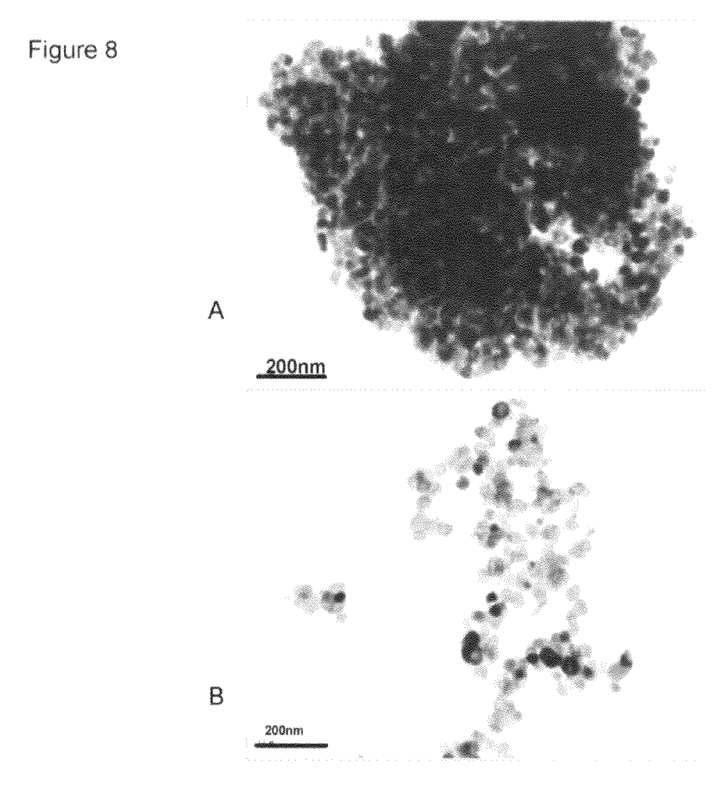
FIG. 8. shows TEM images of the USP nano-anatase base doped with 0.3 weight percent of phosphorus, prepared at 720° C. for 10 hours, before (A) and after (B) wet milling.

The dry titanium hydrate paste from the Example 3, doped with 0.3 weight percent of phosphorus, was calcined at 720° C. for 10 hours. The calcined material passed the USP specifications, including LOI. FIG. 7 shows the XRD pattern of the material. It is phase pure $TiO_2$-anatase crystalline material with the average particle size of 27 nm determined from the XRD pattern by the Scherrer calculation. The nano-base was further wet milled with YSZ 0.5 mm milling media for 60 minutes. FIG. 8A shows a Transmission Electron Micrograph (TEM) of the material before milling. The USP nano-anatase base forms large, lightly sintered aggregates before milling. These clusters of nano-anatase particles are often one micron in size. FIG. 8B shows a TEM image of the dispersed material. The light aggregates were broken apart almost to the primary particles. The size of remaining aggregates was reduced under 50 nm. The specific surface area increased from 30 $m^2/g$ to 45 $m^2/g$. The particle size distribution after milling provided good transparency to the visible light. Surface of the milled material was further treated with silica and alumina coating to eliminate the $TiO_2$ photocatalytic activity, and the product was further dispersed in water and oil. These products can be directly integrated into the sun screens showing high UV light absorption, excellent optical transparency to the visible light and no harmful photocatalytic activity.

What is claimed is:

1. A novel process for manufacturing a high surface area USP grade $TiO_2$ nano-anatase base comprising the steps of:
   a) producing of a P-doped intermediate product by mixing together a clean titanium hydrate with a mineral acid containing phosphorus in the molecule as a phosphorus doping agent, wherein the introduced concentration of phosphorus is in the range from 0.1 to 0.5 weight percent on the $TiO_2$ basis, and
   b) drying and calcination of the P-doped intermediate product, at the calcination temperature in the range from 650° C. to 850° C. and the time of calcination in the range from 1 to 24 hours, wherein the phosphorus concentration in the calcined product is between 0.1 and 0.5 weight percent based on $TiO_2$ and the product of calcination is a high surface area $TiO_2$ in nano-anatase crystal form meeting the USP grade quality wherein:
      i. loss on ignition at 800° C. for 2 hours is less than 1 weight percent,
      ii. specific surface area of the calcined product, determined from the nitrogen adsorption and desorption isotherms at 77 K (BET), is in the range from 20 to 75 $m^2/g$, and
      iii. crystalline size determined from X-ray powder diffraction patterns (XRD) using the Scherrer equation is between 15 and 40 nm.

2. A process of claim 1, wherein the phosphorus concentration in the calcined product is between 0.3 and 0.45 weight percent based on $TiO_2$.

3. A process of claim 1, further comprising wet milling of the $TiO_2$ nano-anatase USP grade base, producing a dispersed product.

4. A process of claim 3, further comprising a surface treatment of the dispersed product to block photocatalytic activity of titanium dioxide, producing a surface treated product.

5. A process of claim 4, further comprising drying of the dispersed and surface treated product, producing a dry product.

6. A process of claim 5, further comprising micronizing of the dry product, producing a micronized product.

7. A process of claim 6, further comprising re-dispersion of the micronized products in alkyl benzoate, oil, aqueous media or a cosmetic composition.

* * * * *